DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED SEPTEMBER 8, 1970

878 O.G. 239

T878,001

METHOD OF PURIFYING VINYL MONOMERS

Clarence C. Dannelly, Rte. 8, Indian Springs 37664, and John R. Caldwell, 404 Colonial Heights Road 37663, both of Kingsport, Tenn.

Filed Dec. 13, 1968, Ser. No. 783,719

Int. Cl. C07c *69/54*

U.S. Cl. 260—486

No Drawing. 18 Pages Specification

Vinyl monomer containing an acidic or basic organic inhibitor of free radical initiation of polymerization, such as a phenolic and amino compound, is treated to remove the inhibitor by contacting said vinyl monomer with an inorganic basic or acidic compound which is insoluble in the monomer but which reacts with the inhibitor to form a removable salt in either solid or liquid phase and thereafter separating the salt thus formed from the monomer. Suitable basic compounds are typified by the alkaline earth oxides and hydroxides and acidic compounds by inorganic acid salts.